United States Patent [19]

Martin

[11] 4,150,036
[45] Apr. 17, 1979

[54] ANTIBIOTIC PENTALENOLACTONE DERIVATIVE

[75] Inventor: David G. Martin, Kalamazoo, Mich.

[73] Assignee: The Upjohn Company, Kalamazoo, Mich.

[21] Appl. No.: 915,615

[22] Filed: Jun. 15, 1978

[51] Int. Cl.$^2$ .............................................. C07D 311/94
[52] U.S. Cl. .................................. 260/343.21; 424/279
[58] Field of Search ................................... 260/343.21

[56] References Cited

U.S. PATENT DOCUMENTS 4,083,997   4/1978   Houlihan ........................ 260/343.21

OTHER PUBLICATIONS

Chemical Abstracts 8th collective 22540S.
Chemical Abstracts 9th collective 27073CS.

*Primary Examiner*—Natalie Trousof
*Assistant Examiner*—Jane T. Fan
*Attorney, Agent, or Firm*—Roman Saliwanchik

[57] ABSTRACT

Novel antibiotic U-36,699 which has been identified as the α-methylene derivative of pentalenolactone. Antibiotic U-36,699 has the following structural formula

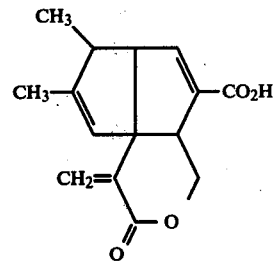

This antibiotic is produced in a chemical process using pentalenolactone (also known as antibiotic P.A. 132), as the starting material. Antibiotic U-36,699 is active against *Staphylococus aureua, Sarcina lutea, Mycobacterium phlei, Mycobacterium avium, Saccharomyces cerevisiae,* and *Penicillium oxalicum.* Thus, antibiotic U-36,699 can be used in various environments to eradicate or control such fungi and bacteria. Further, antibiotic U-36,699 inhibits P 388 leukemia cells in laboratory mice. Thus, this antibiotic can be used to treat laboratory mice harboring P 388 leukemia cells.

2 Claims, No Drawings

ANTIBIOTIC PENTALENOLACTONE DERIVATIVE

The invention described herein was made in the course of, or under Contract PH 43-68-1023 with the National Cancer Institute, National Institutes of Health, Bethesda, MD 20014.

BACKGROUND OF THE INVENTION

Antibiotic P.A. 132, and a microbiological process for its preparation, are disclosed in U.S. Pat. No. 3,113,074. The antibiotic is produced in a fermentation process using the microorganism *Streptomyces roseogriseus,* which has been deposited with the ATCC culture repository and given the accession number ATCC 12414. A subculture of this deposit is available to the public upon request to the American Type Culture Collection, Washington, D.C.

The structure of antibiotic P.A. 132 is disclosed in the paper entitled "The Structure And Absolute Configuration Of Pentalenolactone (PA 132)", by D. G. Martin et al., Tetrahedron Letters No. 56, pages 4901-4904, 1970.

The structure of P.A. 132 is as follows:

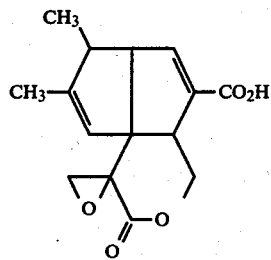

BRIEF SUMMARY OF THE INVENTION

The novel antibiotic of the invention, U-36,699, is obtained by a chemical process using antibiotic P.A. 132 as the starting material. Advantageously, the process is conducted by reacting P.A. 132 with chromous chloride to effect a reduction of the epoxide group.

DETAILED DESCRIPTION OF THE INVENTION

Antibiotic U-36,699 is produced by reacting a preparation of antibiotic P.A. 132 with a reducing agent, for example, chromous chloride (preferred) or sodium 0,0-diethyl phosphorotelluroate. Advantageously, the reaction is conducted under a nitrogen atmosphere. The desired product is isolated from the reaction mixture by first extracting the mixture with a suitable solvent, for example, methylene chloride. The extracts are washed with brine, dried and then evaporated under reduced pressure to give a viscous oil containing the desired product. This oil can be chromatographed on a silica gel column (Merck Darmstadt) using a solvent system consisting of benzene: HOAC: 95% EtOH (100:1:1) to develop the column. Eluted fractions are subjected to thin layer chromatography (tlc) on silica gel plates (Whatman LK5DF) developed with $CH_2Cl_2$:iPrOH:-HOAC (100:1:1). The fractions displaying a zone having the same mobility as U-36,699 when examined under UV light of 220-254 nm are evaporated to dryness under reduced pressure. Thorough drying leaves a crystalline residue of the desired compound. Crystallization of antibiotic U-36,669 can be accomplished from a suitable solvent system, for example, benzene-petroleum ether (Skellysolve B or isomeric hexanes). The crystals of antibiotic U-36,699 obtained from this crystallization can be subjected to a recrystallization process from the same solvent system to afford an essentially pure crystalline preparation of antibiotic U-36,699.

The chromatographic purification of crude antibiotic U-36,699 can also be carried out on silica gel using 1% acetic acid in methylene chloride as a solvent system. The subsequent crystallization of antibiotic U-36,699 can also be conducted using toluene-cyclohexane.

Since antibiotic U-36,699 is an acidic compound, salts of antibiotic U-36,699 can be made with inorganic or organic bases. The antibiotic U-36,699 salts can be prepared by suspending U-36,699 free acid in water, adding a dilute base until the pH of the mixture is about 7 to 8, and freeze-drying the mixture to provide a dry residue consisting of the U-36,699 salt. Antibiotic U-36,699 salts which can be formed include sodium, potassium, and calcium. Other salts of antibiotic U-36,699 can be formed with an organic base, such as primary, secondary and tertiary amines. The following compounds are illustrative of such bases: triethylamine, procaine, benzylamine, dibenzylamine, dibenzylethylene diamine, and the like. Salts of antibiotic U-36,669 can be used for the same purposes as the free acid.

ANTIMICROBIAL SPECTRUM OF ANTIBIOTIC U-36,699

Antibiotic U-36,699 is active against various bacteria and fungi as shown in the following table. The procedures for the tests are as follows:

The MIC was determined by standard bactercidal methods using two-fold dilutions of the antibiotic in Brain Heart Infusion Broth (Difco Lab., Detroit, Mich.). The inocula are overnight cultures of the test organisms, diluted so that the final population contains approximately $10^5$ cells/ml. The tubes are incubated at 28°-37° C. for 42 hours. The MIC is determined by transferring 0.1 ml of broth from 42 hour tubes showing no growth into 10 ml of antibiotic free broth; tubes with no growth in 24 hours are considered to have contained bactercidal concentrations. An excellent broth for the fungi contains: $KH_2PO_4$, 0.5%, dextrose, 3.0%; yeast extract, 0.7%.

| Microorganism | Minimum Inhibitory Concentration (mcg/ml) | | |
|---|---|---|---|
| | 24 hrs. | 48 hrs. | 72 hrs. |
| *Bacteria:* | | | |
| *Staphylococcus aureus* | 100 | >100 | |
| *Bacillus subtilis* | >100 | >100 | |
| *Sarcina lutea* | 50 | 100 | |
| *Escherichia coli* | >100 | >100 | |
| *Proteus vulgaris* | >100 | >100 | |
| *Klebsiella pneumoniae* | >100 | >100 | |
| *Mycobacterium phlei* | | | 3.12 |
| *Mycobacterium avium* | | 25 | 50 |
| *Fungi:* | | | |
| *Saccharomyces cerevisiae* | | 250 | 1000 |
| *Saccharomyces pastorianus* | 1000 | >1000 | |
| *Candida albicans* | >1000 | >1000 | |
| *Penicillium oxalicum* | | 125 | 1000 |

Antibiotic U-36,699 is active against *Mycobacterium avium* and, thus, can be used to control this microorganism which is a known producer of generalized tuberculosis in birds and rabbits. Also, antibiotic U-36,669, or its salts, can be used to disinfect washed and stacked food utensils contaminated with *S. aureus.* Further, antibiotic U-36,699, or its salts, can be used as an industrial preservative, for example, as a bacteriostatic rinse for laundered clothes and for impregnating paper and fabrics; and, it is useful for suppressing the growth of sensitive organisms in plate assays and other microbiological media.

The following example is illustrative of the process and product of the present invention, but is not to be construed as limiting. All percentages are by weight, and the solvent mixture proportions are by volume unless otherwise noted.

EXAMPLE 1

A preparation of antibiotic P.A. 132 obtained as described in U.S. Pat. No. 3,113,074, Examples 1 and 2, (15.8 g) containing approximately 5 g of P.A. 132, is dissolved in 200 ml of glacial acetic acid. While stirring the resulting solution under an atmosphere of $N_2$, 200 ml of aqueous chromous chloride (Fisher Scientific SO-C 169) is added. The resulting mixture (slight warming observed after the addition) is stirred for one hour, diluted to 2.5 liters with ice water, and extracted with four-600 ml portions of methylene chloride. The extracts are washed with brine, dried over $MgSO_4$, and evaporated under reduced pressure to give 13.1 g of a viscous oil containing the desired product. This oil is chromatographed on 1.5 kg of silica gel (Merck Darmstadt) with benzene: HOAC: 95% EtOH (100:1:1) as the developing solvent system. Fractions of 450 ml are collected. Tlc indicates that fractions 32–38 contain the desired α-methylene lactone. These fractions are evaporated to dryness, and the residue is thoroughly dried to give a crystalline residue of the desired product. Crystallization of antibiotic U-36,699 from benzene-petroleum ether (Skellysolve B) affords 3.79 g of the crystalline lactone having a melting point of 152.5°–160.5°. Recrystallization from the same solvent pair yields 3.21 g of essentially pure crystalline antibiotic U-36,699 having a melting point of 161°–166°.

Anal. Calcd. for $C_{15}H_{16}O_4$: C, 69.21; H, 6.20. Found : C, 68.95; H, 6.37.

$\alpha_D^{25}$ in $CHCl_3 = -217$ (3 samples range $-217$ to $-223$).

UV end absorption with a shoulder at 214 nm (a 47.09 ∈ 12,250).

I claim:

1. Antibiotic U-36,699 which has the following structural formula:

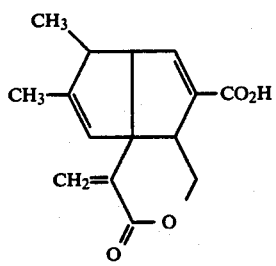

2. Base addition salts of antibiotic U-36,699, said antibiotic as described in claim 1.

* * * * *